(12) United States Patent
Hanselmann et al.

(10) Patent No.: US 7,348,450 B2
(45) Date of Patent: *Mar. 25, 2008

(54) METHOD FOR THE PRODUCTION OF 6,6,6-TRIHALO-3,5-DIOXOHEXANOIC ACID ESTERS

(75) Inventors: Paul Hanselmann, Brig-Glis (CH); Wolfgang Wenger, Ballwald (CH)

(73) Assignee: Lonza Ltd., Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/416,212

(22) Filed: May 3, 2006

(65) Prior Publication Data

US 2006/0235240 A1  Oct. 19, 2006

Related U.S. Application Data

(63) Continuation-in-part of application No. PCT/EP04/11970, filed on Apr. 24, 2006.

(30) Foreign Application Priority Data

Oct. 24, 2003  (EP)  .................................. 03024344

(51) Int. Cl.
  C07C 69/74  (2006.01)
  C07C 69/66  (2006.01)
(52) U.S. Cl. ....................... 560/126; 560/174
(58) Field of Classification Search ................ 560/174, 560/126
See application file for complete search history.

(56) References Cited

U.S. PATENT DOCUMENTS 6,399,339 B1 *  6/2002  Wolberg et al. ............ 435/126
2002/0058690 A1  5/2002  Li et al.

FOREIGN PATENT DOCUMENTS

| JP | 06-049039 | 2/1994 |
|----|-----------|--------|
| WO | 94/11361  | 5/1994 |
| WO | 02/02547  | 1/2002 |
| WO | WO02055519 | 7/2002 |

OTHER PUBLICATIONS

Tetsuro Shimo, Kenichi Somekawa, et al., "3-(2H-Pyran-2-on-6-yl) indolizines and the Diels-Alder Reactions with Some Olefinic and Acetylenic Dienophiles." Journal of Hetrocyclic Chemistry, vol. 28, 1991, pp. 1831-1833.
G. Solladie, et al., "Chiral Sulfoxides in Asymmetric Synthesis," Tetrahedron: Asymmetry, vol. 7, No. 8, 1996, pp. 2371-2379.
W.T. Brady, et al., "The Synthesis of Pyranones Utilizing the (4+2) Cycloaddition of Ketenes and Siloxy Dienes," Journal of Heterocyclic Chemistry, vol. 20, 1983, pp. 501-506.
Batelaan, J. G., Synthetic Commun. 1976, vol. 6, pp. 81-83.
Solladie, et al., Tetrahedron: Asymmetry, 1996, vol. 7, pp. 2371-2379.
Effenberger, F., et al., Chem. Ber., 1984, vol. 117, pp. 3270-3279.

* cited by examiner

*Primary Examiner*—Yvonne Eyler
*Assistant Examiner*—Jennifer Y Cho
(74) *Attorney, Agent, or Firm*—Fisher, Christen & Sabol

(57) ABSTRACT

A method for the production of 6,6,6-trihalo-3,5-dioxohexanoic acid esters of formula (I):

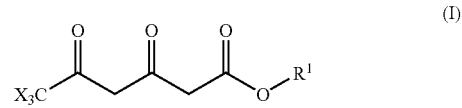

in addition to the enols thereof and *E* and *Z* isomers, wherein X independently represents fluorine, chlorine or bromine and $R^1$ represents alkyl, cycloalkyl, aryl or aralkyl. A method for the production of enol ethers of formula (Ib):

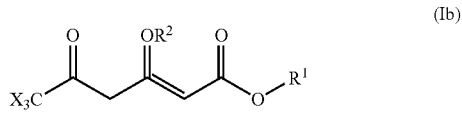

and the enols thereof (E and Z isomers) wherein X and $R^1$ have the above-mentioned meanings.

3 Claims, No Drawings

METHOD FOR THE PRODUCTION OF 6,6,6-TRIHALO-3,5-DIOXOHEXANOIC ACID ESTERS

This application is a continuation-in-part of the 371 national stage application, filed on Apr. 24, 2006, of International (PCT) Application No. PCT/EP04/011970, filed on Oct. 22, 2004, that has priority benefit of European Patent Application No. 03024344.8, filed on Oct. 24, 2003.

The invention relates to a method for preparing 6,6,6-trihalo-3,5-dioxohexanoic esters of the formula

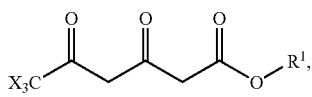
I and the enols and E and Z isomers thereof
or
the enol ethers thereof, of the formula

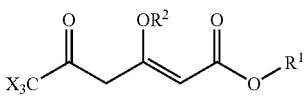
Ib and the enols and E and Z isomers thereof in which the substituents X are each independently of one another fluorine, chlorine or bromine, and in which $R^1$ is in each case alkyl, cycloalkyl, aryl or aralkyl, and $R^2$ is alkyl, cycloalkyl, allyl or benzyl, starting from pyranones of the formula

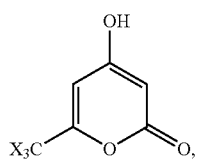
II in which X has the abovementioned meaning.

Ethyl 6,6,6-trihalo-3,5-dioxohexanoates of the formula I are employed for example for the production of herbicides and agrochemicals (JP-A-06-049039).

Known methods for synthesizing substituted tricarbonyl compounds having a 3,5-dioxohexanoic ester basic structure start for example from ethyl acetoacetate, which is condensed with ethyl benzoate in THF in the presence of KH/BuLi (WO-A-94/11361), or with a highly substituted 3-oxopentanamide in THF in the presence of NaH/BuLi (WO-A-02/055519).

A method for preparing tert-butyl 6,6,6-trifluoro-3,5-dioxohexanoate from 2,2,2-trifluoroethyl trifluoroacetate and tert-butyl acetoacetate is disclosed in WO-A-02/02547.

A further alternative variant for preparing substituted tricarbonyl compounds proceeds by ring opening of a pyranone such as, for example, of dehydracetic acid, which is converted by means of $Mg(OMe)_2$ in methanol into methyl 3,5-dioxohexanoate (Batelaan, J. G., Synthetic Commun. 1976, 6, 81-83).

These known methods have the disadvantage that costly reagents such as BuLi are used.

Solladié, et al., *Tetrahedron: Asymmetry* 1996, 7, 2371-2379, disclosed that ring opening of dehydracetic acid of the formula

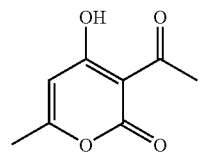

to give the tricarbonyl compound is possible, but leads to elimination of the acetyl substituent previously introduced during the synthesis. However, a loss of mass has disadvantageous effects on the profitability of a method in industrial process management.

It was therefore an object of the present invention to provide a simple method for preparing alkyl 6,6,6-trihalo-3,5-dioxohexanoates and the enols and enol ethers thereof, which can utilize easily obtainable pyrones as starting compounds.

This object is achieved according to the invention by the method of the invention.

It has been found that compounds of the formula

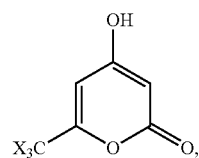
II in which the substituents X are each independently of one another fluorine, chlorine or bromine, provide, after conversion of the hydroxyl group into an ether group and subsequent opening of the pyran ring with a metal alcoholate, depending on the further reaction conditions, compounds of the formula I or the enol ethers thereof of the formula Ib in good yield.

The present method is distinguished by no loss of mass occurring during the ring opening, and the number of carbon atoms present in the basic structure being maintained.

The method of the invention is surprising because it is known that 4-hydroxypyran-2-one cannot be converted into the open-chain tricarbonyl compound by reaction with sodium methanolate but, on the contrary, as shown in the reaction equation below is firstly methylated on the hydroxyl group and then the pyranone ether is converted into a phloroglucinol derivative (Effenberger, F., et al., Chem. Ber. 1984, 117, 3270-3279).

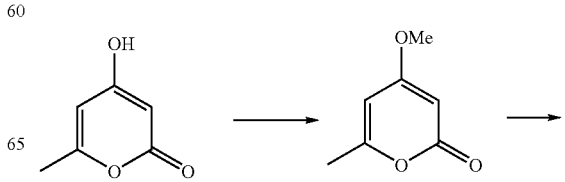

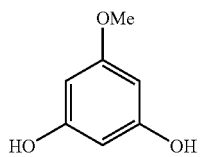

It was thus not possible to expect the ring opening resulting in the method of the invention. Tetsuro, S., et al., discloses the formation of 6-tribromo-4-methoxypyran-2-one as unwanted byproduct of a bromination reaction of 4-methoxy-6- methylpyran-2-one with N-bromosuccinimide (NBS) in a yield of only 5 percent.

The starting compounds of the formula II of the method of the invention can easily be obtained. Thus, for example, 4-hydroxy-6-trifluoromethylpyran-2-one can be prepared by reacting trifluoroacetic acid with ketene.

Alkyl means here and hereinafter in particular an optionally halogen-substituted, linear or optionally branched group having 1 to 8 carbon atoms, such as, for example, methyl, ethyl, propyl, isopropyl, n-butyl, isobutyl, sec-butyl, tert-butyl, pentyl, hexyl, heptyl, octyl.

Cycloalkyl means here and hereinafter in particular a cyclic group having 3 to 8 carbon atoms, such as, for example, cyclopropyl, cyclobutyl, cyclopentyl, cyclohexyl, cycloheptyl, cyclooctyl.

Aryl means here and hereinafter in particular an optionally alkyl- and or halogen-substituted aromatic group having 6 or 8 carbon atoms, such as, for example, phenyl, p-tolyl or naphthyl.

Aralkyl means here and hereinafter in particular an alkyl group substituted by an aryl group, such as, for example, phenylethyl, where the alkyl group comprises 1 to 4 carbon atoms, and the aryl group is an optionally halogen-substituted, aromatic or heteroaromatic group having 4 to 8 carbon atoms, such as, for example, phenyl, naphthyl, 2- or 3-furanyl, 2- or 3-thiophenyl or 2-, 3- or 4-pyridinyl.

In the method of the invention for preparing compounds of the formula

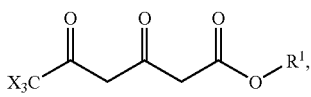

I and the enols and E and Z isomers thereof or the enol ethers thereof of the formula

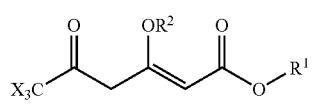

Ib and the enols and E and Z isomers thereof in which the substituents X are each independently of one another fluorine, chlorine or bromine, and in which $R^1$ is in each case alkyl, cycloalkyl, aryl or aralkyl, and $R^2$ is alkyl, cycloalkyl, allyl or benzyl, compounds of the formula

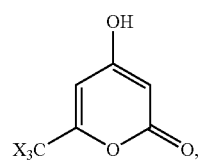

II in which X has the aforementioned meaning, are converted by reacting the hydroxyl group with a compound of the formula $(R^2O)_2SO_2$ or with a compound of the formula $Y-R^2$ in which Y is tosyl, chlorine, bromine or iodine, and in which $R^2$ in each case has the abovementioned meaning, into a compound of the formula

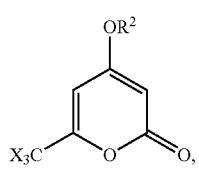

III in which $R^2$ and X have the stated meanings, and the pyranone ring of the reaction product is subsequently opened by reaction with a metal alcoholate of the formula $R^1O^-1/nM^{n+}$ in which $R^1$ has the abovementioned meaning, and $M^{n+}$ is an alkali metal or alkaline earth metal cation and n=1 or 2, depending on the further reaction conditions, to give compounds of the formula I or Ib.

Suitable reagents for the preparation according to the invention of compounds of the formula III are for example dimethyl sulfate, diethyl sulfate, methyl iodide, ethyl bromide, methyl tosylate, ethyl tosylate, phenyl tosylate, allyl chloride, allyl bromide, benzyl chloride or benzyl bromide.

$M^{n+}$ in the metal alcoholates of the formula $R^1O^-1/nM^{n+}$ is preferably $Li^+$, $Na^+$, $K^+$, $Mg^{2+}$ or $Ca^{2+}$.

If a strong acid is added (pH<1) to the reaction mixture of compounds of the formula III after addition of the metal alcoholate, and the mixture is reacted further, compounds of the formula I and enols thereof can be obtained. In this method, the radical $R^2$ is eliminated. If a weak acid, or no acid at all, is added to the reaction mixture of compounds of the formula III after addition of the metal alcoholate, and the mixture is reacted further, enol ethers of the formula Ib and enols thereof can be obtained. In this variant of the method, the radical $R^2$ is retained.

The enol ethers of the formula Ib can likewise be converted into compounds of the formula I and enols thereof in poor yields after addition of strong acids and under strongly acidic conditions with elimination of the radical $R^2$.

Strong acids mean in the method of the invention for example HCl, HBr, HI, $H_2SO_4$, trifluoroacetic acid or solid acids such as, for example, acidic zeolites such as H-ZSM-5 or acidic sheet silicates.

Weak acids mean in the method of the invention for example acetic acid and dilute aqueous HCl, $H_3PO_4$ or $H_2SO_4$ acids or addition of strong acids after previous addition of water.

In a preferred embodiment, compounds of the formula III are converted into compounds of the formula I in which X is fluorine and $R^1$ is $C_{1-8}$-alkyl, with elimination of the radical $R^2$. In a further preferred embodiment, $R^1$ is $C_{1-4}$-alkyl. In a particularly preferred embodiment, $R^1$ is methyl.

Compounds of the formula I in the method of the invention also means the corresponding enols such as, for example, of the formulae

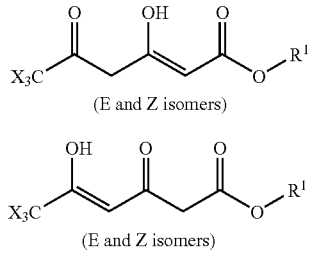

(E and Z isomers)

singly or as mixture, and are also encompassed by the invention. The equilibrium distribution of compounds of the formula Ia to the enol forms thereof (as E and Z isomers) is influenced by various influences such as, for example, the solvent, the temperature or optionally by protonating or deprotonating additions. After kugelrohr distillation, for example, compound Ia with X=fluorine and $R^1$=methyl without solvent is predominantly in the form of the monoenol of the formula Ia' at room temperature.

The enols of compounds of the formula I differ from one another by the enolized carbonyl group and the location and orientation of the resulting double bond(s). The carbonyl groups at $C^3$ and/or $C^5$ may be enolized. It is possible in this connection for there to be a double bond in each case between carbon atoms $C^2/C^3$, $C^3/C^4$, $C^4/C^5$ or conjugated double bonds between $C^2/C^3$ and $C^4/C^5$, and the double bonds may additionally be in the E or Z configuration. The enols are usually in the form of mixtures of a plurality of forms.

The invention likewise encompasses compounds of the formula:

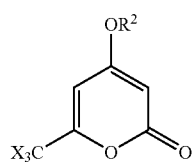

in which X is in each case independently of one another F, Cl or Br, and in which $R^2$ is alkyl, cycloalkyl, allyl or benzyl, with the exception of the compound in which X is bromine and $R^2$ is methyl.

Likewise encompassed by the invention are enol ethers of the formula

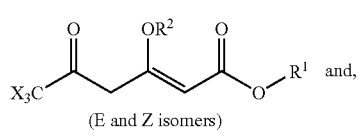

(E and Z isomers)

and enols thereof, such as, for example

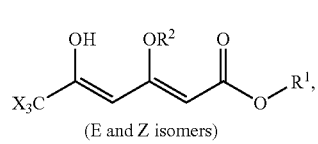

(E and Z isomers)

in which X is in each case independently of one another F, Cl or Br, and in which $R^1$ is alkyl, cycloalkyl, aryl or aralkyl, and in which $R^2$ is alkyl, cycloalkyl, allyl or benzyl. The compounds of the formula Ib may, just like the compounds of the formula I described above, be in the form of E and/or Z isomers. Depending on the external conditions, however, only the carbonyl group at $C^5$ may be enolized. The number and location of the resulting double bonds at $C^2/C^3$ and/or $C^4/C^5$ correspond to the E and Z isomers of the enols of the compounds of the formula I.

Alkyl 3,3,3-trihalo-3,5-dioxohexanoates can be prepared by the method described above from 4-methoxy-6-trihalomethylpyran-2-ones. Preferably, methyl 6,6,6-trifluoro-3,5-dioxo-hexanoate is prepared from 4-methoxy-6-trifluoromethylpyran-2-one.

The invention also includes compounds of formula:

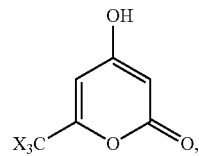

in which X is in each case independently of one another F or Cl, and in which $R^2$ is selected from the group consisting of alkyl, cycloalkyl and benzyl.

The invention also includes compounds of formula:

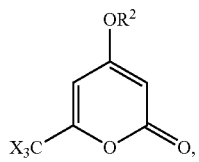

in which X is in each case independently of one another F or Cl, and in which $R^2$ is selected from the group consisting of ethyl, propyl, isopropyl, n-butyl, isobutyl, sec-butyl, tert-butyl, hexyl, and octyl.

The invention further includes compounds of formula:

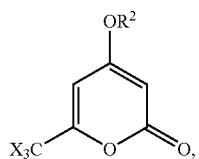

in which X is in each case independently of one another F or Cl, and in which R² is selected from the group consisting of ethyl, propyl, isopropyl, n-butyl, isobutyl, sec-butyl, tert-butyl, hexyl, heptyl, octyl, cyclopropyl, cyclobutyl, cyclopentyl, cyclohexyl, cycloheptyl, cyclooctyl, and benzyl.

The invention also includes compounds of formula:

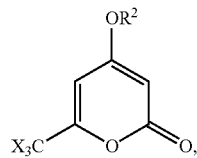

III in which X is in each case independently of one another F, Cl or Br, and in which R² is selected from the group consisting of ethyl, propyl, isopropyl, n-butyl, isobutyl, sec-butyl, tert-butyl, pentyl, hexyl, heptyl, octyl, cyclopropyl, cyclobutyl, cyclopentyl, cyclohexyl, cyclooctyl, and benzyl.

The invention also includes compounds of formula:

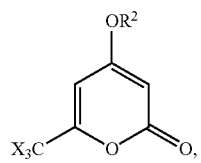

III in which X is in each case independently of one another F or Cl, and in which R² is methyl, ethyl, propyl, isopropyl, n-butyl, isobutyl, sec-butyl, tert-butyl, pentyl, hexyl, heptyl, octyl, cyclopropyl, cyclobutyl, cyclopentyl, cyclohexyl, cyclooctyl, or benzyl.

EXAMPLES

The following examples illustrate the procedure for the method of the invention without this being regarded as a restriction.

Example 1

4-Methoxy-6-trifluoromethylpyran-2-one (III; R²=methyl, X=fluorine)

Sodium carbonate (1.35 g, 13 mmol) and dimethyl sulfate (2.17 g, 17 mmol) were added to a solution of 4-hydroxy-6-trifluoromethylpyran-2-one (3.0 g, 17 mmol) in acetone (50 mL). The mixture was heated under reflux for 3 hours and, after cooling, filtered. Concentration of the filtrate resulted in 2.9 g of crude product as a brown oil. It was possible to obtain 4-methoxy-6-trifluoromethylpyran-2-one (2.74 g, 14 mmol, 83%) as colorless needles with a melting point of 61° C. by crystallization from hexane.

¹H NMR (400 MHz, DMSO-d₆) δ: 7.01 (d, J=1.6 Hz, 1H), 5.98 (d, J=1.6 Hz, 1H), 3.7 (s, 3H).

Example 2

Methyl 6,6,6-trifluoro-2-methoxy-5-oxo-2-hexenoate (Ib; R¹=R²=methyl, X=fluorine)

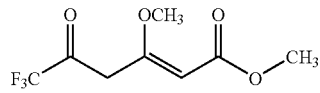

and the enols and E and Z isomers thereof

A solution of 4-methoxy-6-trifluoromethylpyran-2-one (2.7 g, 14 mmol) in a methanolic magnesium methanolate solution (8.5% Mg(OMe)₂, 8.36 g, 8 mmol) was heated under reflux for 16 hours. The solution was concentrated and taken up in water and ethyl acetate, and the organic phase was brought to pH 5 by adding dilute hydrochloric acid. The organic phase was separated off, dried and concentrated. 1.5 g of crude product were obtained as a yellow oil. Kugelrohr distillation at 0.04 mbar and about 160° C. afforded methyl 6,6,6-trifluoro-3-methoxy-5-oxo-2-hexenoate (1.50 g, 6.6 mmol, 48%) as a pale yellow oil.

Data for the main compound: ¹H NMR (400 MHz, DMSO-d₆) δ (resonance lines of the enol form Ib, without E/Z determination): 6.05 (s, 1H), 3.9 (s, 3H), 3.82 (s, 2H), 3.62 (s, 3H). ¹⁹F-NMR (386 MHz, DMSO-d₆) δ: −76.8. MS: 227 [M+H]⁺.

Example 3

Methyl 6,6,6-trifluoro-3,5-dioxohexanoate (I; R¹=methyl, X=fluorine)

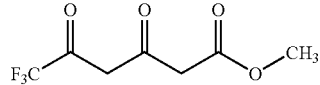

and the enols and E and Z isomers thereof

A solution of 4-methoxy-6-trifluoromethylpyran-2-one (10 g, 52 mmol) in a methanolic magnesium methanolate solution (8.5% Mg(OMe)₂, 62.8 g, 61 mmol) was heated under reflux for 2 hours. Concentrated aqueous HCl (25.5 g, 250 mmol) was added to the reaction solution, and the mixture was heated under reflux for a further 2 hours, then cooled and concentrated in vacuo to about 20% of the initial volume. The residue was mixed with 10 mL each of methylene chloride and water. The organic phase was separated off, washed with water, dried over sodium sulfate and concentrated. Kugelrohr distillation at 0.04 mbar and about 160° C. afforded methyl 6,6,6-trifluoro-3,5-dioxohexanoate (2.8 g, 13 mmol, 26%) as a pale yellow oil.

Data for the main compound:

¹H NMR (400 MHz, DMSO-d₆) δ (resonance lines of the enol form Ia', without E/Z determination): 6.0 (br, 2H), 3.8 (s, 2H), 3.65 (s, 3H).

¹³C-NMR (100 MHz, DMSO-d₆) δ (resonance lines of the enol form Ia', without E/Z determination): 181.6 (s), 167.7 (s), 116.9 (q, ¹J_{C-F} 286 Hz), 95.9 (t), 52.0 (q), 49.7 (t), C-3 not identifiable. MS: 212 (M⁺).

The invention claimed is:

1. A method for preparing a compounds of formula:

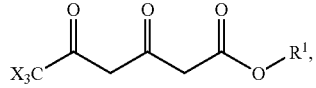

or an enol thereof, or an E or Z isomer thereof, in which X is in each case independently of one another fluorine, chlorine or bromine, and in which $R^1$ is alkyl, cycloalkyl, aryl or aralkyl, comprising (a) initially converting a compound of formula:

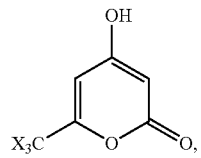

in which X has the stated meaning, by reacting the hydroxyl group of the compound of formula II with a compound of the formula $(R^2O)_2SO_2$ or with a compound of the formula $Y-R^2$ in which Y is tosyl, chlorine, bromine or iodine, and in which $R^2$ is in each case alkyl, cycloalkyl, or benzyl, into a compound of formula:

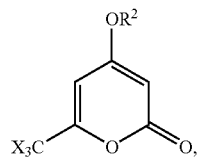

in which $R^2$ and X each has the above mentioned meaning, and (b) converting the compound of formula III by reaction with a metal alcoholate of the formula $R^1O^-1/nM^{n+}$ in which $R^1$ has the above-mentioned meaning and $M^{n+}$ is an alkali metal or alkaline earth metal cation and n=1 or 2, and (c) further treating with a strong acid, into a compound of formula I and/or an enol thereof and/or an E or Z isomer thereof.

2. A method for preparing an enol ether of the formula:

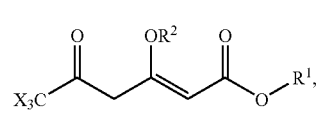

or an enol thereof or, in each case, the E or Z isomer thereof, in which X is in each case independently of one another F, Cl or Br, and in which $R^1$ is alkyl, cycloalkyl, aryl or aralkyl, and $R^2$ is alkyl, cycloalkyl, allyl or benzyl, comprising (a) initially converting a compound of the formula:

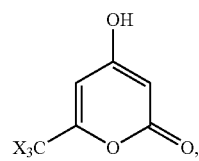

in which X has the stated meaning, by reaction of the hydroxyl group of the compound of formula II with a compound of the formula $(R^2O)_2SO_2$ or with a compound of the formula $Y-R^2$ in which Y is tosyl, chlorine, bromine or iodine, and in which $R^2$ in each case has the above-mentioned meaning, into a compound of the formula:

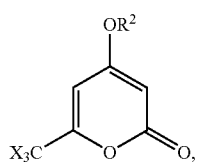

in which $R^2$ and X each has the above-mentioned meaning, and (b) converting the compound of formula III by reaction with a metal alcoholate of the formula $R^1O^-1/nM^{n+}$ in which $R^1$ is alkyl, cycloalkyl, aryl or aralkyl and $M^{n+}$ is an alkali metal or alkaline earth metal cation and n=1 or 2, and (c) optionally further treating with a weak acid or, after addition of water, a strong acid into an enol ether of the formula Ib and/or an enol thereof.

3. The method in claim 2 wherein conversion product of step (b) is further treated, step (c), with the weak acid into the enol ether of formula Ib and/or the enol thereof.

* * * * *